United States Patent [19]

Beck et al.

[11] Patent Number: 5,175,336

[45] Date of Patent: Dec. 29, 1992

[54] FLUOROMETHYLATED POLYCYANOBENZENES, THEIR ALKALI METAL CYANIDE ADDUCTS, PROCESSES FOR THEIR PREPARATION AND USE OF THE FLUOROMETHYLATED POLYCYANOBENZENES

[75] Inventors: Gunther Beck, Leverkusen; Wolfgang von der Emden, Bergisch Gladbach; Helmut Heitzer, Leverkusen; Friedrich W. Kröck, Odenthal; Ernst Kysela, Bergisch Gladbach; Albrecht Marhold, Leverkusen, all of Fed. Rep. of Germany

[73] Assignee: Bayer Aktiengesellschaft, Leverkusen, Fed. Rep. of Germany

[21] Appl. No.: 701,540

[22] Filed: May 16, 1991

[30] Foreign Application Priority Data

May 26, 1990 [DE] Fed. Rep. of Germany ....... 4016993
Jul. 18, 1990 [DE] Fed. Rep. of Germany ....... 4022751

[51] Int. Cl.⁵ ................. C07C 253/14; C07C 255/51
[52] U.S. Cl. .................................. 558/343; 558/419; 558/431
[58] Field of Search ................. 558/419, 343, 431

[56] References Cited

U.S. PATENT DOCUMENTS

| | | | |
|---|---|---|---|
| 3,290,353 | 12/1966 | Battershell et al. | 558/419 |
| 3,737,449 | 6/1973 | Eilingsfeld et al. | 558/419 |
| 3,816,505 | 6/1974 | Watts, Jr. | 558/419 |
| 3,975,424 | 8/1976 | Fujii et al. | 558/419 |
| 4,517,129 | 5/1985 | Milner | 260/465 C |
| 4,614,742 | 9/1986 | Ishikawa et al. | 558/419 X |
| 5,021,605 | 6/1991 | Kobayashi et al. | 558/419 X |

FOREIGN PATENT DOCUMENTS 3718641 12/1988 Fed. Rep. of Germany .
1026290 4/1966 United Kingdom ................ 558/419

OTHER PUBLICATIONS

C.A. 88:62120q, Yogupol'skii et al. (1977).

*Primary Examiner*—Joseph Paul Brust
*Attorney, Agent, or Firm*—Sprung Horn Kramer & Woods

[57] ABSTRACT

The invention relates to new fluoromethylated polycyanobenzenes of the formula

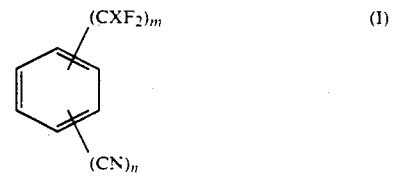

in which
X represents hydrogen, fluorine or chlorine,
m is 1 or 2 and
n is (6−m), to a process for their preparation and to the salt-like alkali metal cyanide adducts of the fluoromethylated polycyanobenzenes formed as intermediates in this preparation process and to the use of the fluoromethylated polycyanobenzenes for the detection of anions.

5 Claims, No Drawings

FLUOROMETHYLATED POLYCYANOBENZENES, THEIR ALKALI METAL CYANIDE ADDUCTS, PROCESSES FOR THEIR PREPARATION AND USE OF THE FLUOROMETHYLATED POLYCYANOBENZENES

The invention relates to new fluoromethylated polycyanobenzenes, a process for their preparation, the salt-like alkali metal cyanide adducts of the fluoromethylated polycyanobenzenes formed as intermediates in this preparation process and to the use of the fluoromethylated polycyanobenzenes for the detection of anions.

New fluoromethylated polycyanobenzenes of the formula

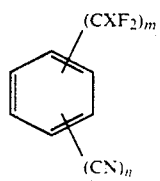

(I)

have been found, in which
X represents hydrogen, fluorine or chlorine,
m is 1 or 2 and
n is $(6-m)$.

The invention furthermore relates to a process for the preparation of the fluoromethylated polycyanobenzenes of the formula (I), according to which fluoromethylated fluorobenzenes of the formula

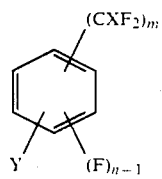

(II)

in which,
X, m and n have the meaning given under formula (I) and
Y represents fluorine or CN diluents to give salt-like adducts of the formula

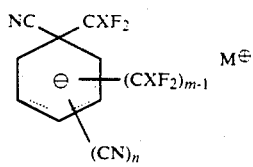

(III)

in which X, m and n have the meaning given under formula (I) and M⊕ represents an alkali metal cation, and this adduct, if desired without isolating it, is converted to the compounds of the formula (I) by treating with acids or by heating to temperatures of 150°–300° C., preferably in vacuo.

The invention furthermore relates to the salt-like adducts of the formula (III).

In the first reaction step of the process according to the invention, the alkali metal cyanides used are preferably the cheap cyanides of sodium or potassium.

The reaction with the alkali metal cyanides is carried out in organic diluents. The organic diluents used are conventional aprotic polar or dipolar solvents. Examples of solvents of this type are:

aliphatic nitriles, such as acetonitrile, propionitrile, 3-methoxypropionitrile; aliphatic and cyclic ethers, such as ethylene glycol dimethyl ether, diethylene glycol dimethyl ether (diglyme), tetrahydrofuran; N,N-dialkylamides of lower aliphatic carboxylic acids, such as N,N-dimethylformamide, N,N-diethylacetamide, N-methylpyrrolidone; aliphatic sulphoxides, such as dimethyl sulphoxide; aliphatic sulphones such as dimethyl sulphone and tetramethylene sulphone; further tetramethylurea, ethylene carbonate, propylene carbonate, N,N,-dimethyl-1,3-imidazolin-2-one and hexamethylphosphoric triamide. Acetonitrile and N,N-dimethylformamide are particularly preferred.

The reaction of the fluoromethylated fluorobenzenes of the formula (II) with the alkali metal cyanides is carried out at temperatures from $-50°$ C. to $+150°$ C., preferably 0° C. to 100° C., particularly preferably 10° C. to 50° C.

The reaction is in general carried out under atmospheric pressure.

The reaction according to the invention of the compounds of the formula (II) with the alkali metal cyanides can be described by the following equations:

(a) when difluoromethylpentafluorobenzene is used:

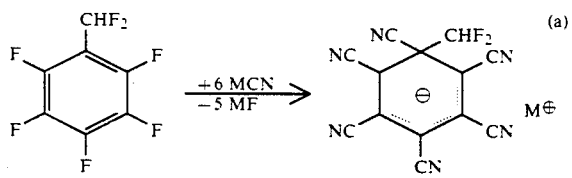

(b) when α,α,α,2,3,5,6-heptafluoro-p-tolunitrile is used:

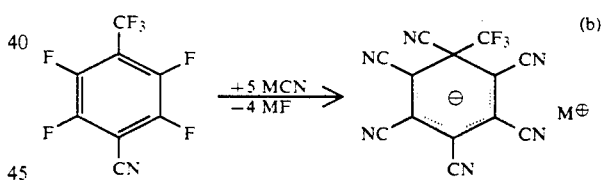

As is evident from the above equations (a) and (b), depending on the number of the fluorine atoms bound to the benzene ring and to be exchanged according to the invention for cyano groups, 5 or 6 mol of alkali metalcyanide are necessary per mole of starting compound (II) in order to prepare the adducts of the formula (III). However, instead of the stoichiometrically required amount of alkali metal cyanide, any desired less than stoichiometric amount of alkali metal cyanide can also be used, since the unconverted starting compounds (II) differ significantly in their solubility properties from the adducts (III) and can therefore be separated off in a simple manner, for example by treatment with solvents, such as dichloromethane, from the adducts of the formula (III) which are completely insoluble in these solvents. The same is true if the reactions described by equations (a) and (b) are iiscontinued before their completion.

Depending on the fluorobenzene of the formula (II) used, the reaction temperatures used and the solvent, the reaction times for the adduct formation vary between an hour and two weeks.

The fluoromethylated fluorobenzenes of the formula (II) required for the process according to the invention as starting compounds are known and described, for example, in J. Fluorine Chem. 1987, 37, pages 1 to 14 or can be prepared by processes known per se.

The reaction according to the invention of the alkali metal cyanides with the compounds of the formula (II) is preferably carried out such that the stoichiometrically required amount of alkali metal cyanide (or a less than stoichiometric amount) is added to the solution of the fluoromethylated fluorobenzene of the formula (II) in the particular anhydrous solvent with exclusion of moisture and with stirring at temperatures from −40° C. to room temperature, and stirring of the mixture at the selected final temperature of, for example, 20° C. to 80° C. is continued until the reaction (which can be easily monitored by gas chromatography) has completely or substantially gone to completion.

If it is desired to isolate the intermediates, i.e. the adducts of the formula (III), the procedure is preferably as follows:

After the reaction of the compounds of the formula (II) with the alkali metal cyanides is completed, any residues which may have remained undissolved are filtered off; the solvent is removed from the filtrate in vacuo under mild conditions (room temperature to 50° C.). To remove any unconverted residual starting compounds (II), the residue is stirred together with a solvent, for example dichloromethane, at room temperature. The orange-red to red alkali metal salts of the formula (III) which remain undissolved after this treatment with solvents are filtered off; the starting material of the formula (II) can be recovered from the filtrate.

The alkali metal salts of the formula (III) are stable compounds at room temperature; they give fluorescent solutions.

The adducts of the formula (III) can be converted to the compounds of the formula (I) either by treating with acids or thermally by heating to temperatures from 150° C. to 300° C., preferably 170° C. to 230° C., preferably in vacuo.

The acids preferably used for cleaving the compounds of the formula (III) are liquid, lower aliphatic carboxylic acids, such as acetic acid, or else inorganic mineral acids, such as hydrochloric acid. Acid cleavage is preferably carried out at room temperature. The compounds of the formula (III) are cleaved by stirring them with the liquid acids until the characteristic red colour of the initially formed solutions has disappeared. The reaction mixture is then diluted with water and the precipitate is filtered off. The acid cleavage can be described by the following equation:

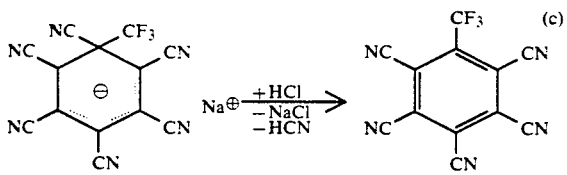

The equation shows that one equivalent of acid is necessary for the cleavage reaction per mole of alkali metal salt of the formula (III). Since the acid can simultaneously be used as reaction medium, the acids are suitable to use 1 to 50 parts by volume of acid per part by weight of alkali metal salt of the formula (III).

For the acid cleavage of the isolated alkali metal salts of the formula (III), the use of 1-normal aqueous hydrochloric acid is particularly preferred.

Depending on the weight ratio used of the alkali metal salt of the formula (III) to the acid and on the concentration of the acid used, the cleavage at room temperature is complete in 0.1 to 24 hours.

Thermal cleavage of the alkali metal salts of the formula (III) is achieved by heating them to temperatures from 150° C. to about 300° C., preferably 170° C. to 230° C. The thermal cleavage is preferably carried out in vacuo (for example in the range from 10 to 0.01 mbar) in a sublimation apparatus. This gives the fluoromethylated polycyanobenzees according to the invention of the formula (I) in pure form. Depending on the type of alkali metal salt of the formula (I) and the selected decomposition temperature, the thermal cleavage requires 0.5 to 24 hours.

The adducts of the formula (III) do not have to be isolated in order to prepare the fluoromethylated polycyanobenzenes according to the invention of the formula (I). The reaction of the starting compounds of the formula (II) with the alkali metal cyanides and the subsequent acid cleavage of the alkali metal salts of the formula (III) formed in this reaction can also be carried out in a kind of "one-pot reaction". To this end, after the first reaction step is complete, about 5 to 10 times the volume of water with respect to the reaction mixture and, at the same time or immediately afterwards, a mineral acid, preferably hydrochloric acid, are added, and the mixture is stirred for 0.5 to 24 hours. The fluoromethylated polycyanobenzenes of the formula (I), which are sparingly soluble in this aqueous medium, are subsequently isolated by filtration. If desired or required, the compounds thus obtained of the formula (I) can be subjected to customary purification operations, such as vacuum sublimation (for example at 200° C./0.1 mbar), recrystallisation and the like.

The smooth course of the reaction of the fluoromethylated polyfluorobenzenes of the formula (II) with alkali metal cyanides to give isolatable, stable adducts of the formula (III) and their conversion to the compounds according to the invention of the formula (I) is extremely surprising, since it is known from the literature that in the reaction of, for example, hexafluorobenzene with sodium cyanide in dimethylformamide no identifiable products are formed; all attempts to isolate hexacyanobenzene were unsuccessful (see J. Chem. Soc. (C), 1966, 708).

Polycyanobenzenes are important starting materials for the preparation of charge-transfer complexes; these CT complexes are distinguished by very good electric conductivity (see, for example, Bull. Acad. Polon. Sci. 23, 563 (1975)). An economical preparation process for this class of compounds is therefore of interest. The fluoromethylated polycyanobenzenes of the formula (I), which have been synthesised here for the first time, give very darkly coloured charge-transfer complexes, for example, with pyrene, which have interesting material properties. Moreover, the polycyanobenzenes of the formula (I) act as biocides, in particular as insecticides and fungicides.

The alkali metal salts of the formula (III) can be incorporated in polymers which then show orange-red fluorescence.

For this purpose, for example, polyacrylonitrile and an alkali metal salt of the formula (III) are dissolved in dimethylfrmamide, and the solvent is then evaporated.

In a similar manner, for example, polyvinyl alcohol and an alkali metal salt of the formula (III) are dissolved in water, and the solvent is then evaporated.

The invention also relates to the use of the fluoromethylated polycyanobenzenes of the formula (I) for visible detection and qualitative and/or quantitative determination of anions.

Although a large number of suitable reagents are known for the detection of cations (see, for example, the dithizones used as reagents for the detection of heavy metal cations), there has been so far a lack of reagents which can be used universally, i.e. which are suitable for the detection of anion of a wide range of acids.

However, it has now been found that the fluoromethylated polycyanobenzenes (I) according to the invention react with anions to form complex anions which strongly absorb light in the visible and/or UV region and are therefore highly suitable for the visual detection and qualitative and quantitative determination of anions.

The visual detection or determination of anions using the fluoromethylated polycyanobenzenes of the formula I to be used according to the invention as test reagents is carried out such that the salts containing the anions to be determined or the solutions of these salts are brought into contact with solutions of the fluoromethylated polycyanobenzenes of the formula I, for example by mixing the salt solutions with a solution of the polycyanobenzenes of the formula I or by spraying the salts (applied to solid supports) with the solutions of the fluoromethylated polycyanobenzenes of the formula I.

Since salts when tested by chromatography differ from one another by their $R_f$ value and the detection of the salts on the stationary phase is often only possible or at least made much easier by their reaction with the fluoromethylated polycyanobenzenes (I), the compounds (I) are highly suitable—of course only after calibration with the salts in question—for qualitative analysis of anions.

Since the adducts obtainable from the fluoromethylated polycyanobenzenes (I) and salts are either strongly coloured and/or show distinct absorption in the UV region, the compounds (I) can also be used after suitable calibration—for the quantitative determination of anions, for example by colorimetry.

Accordingly, the invention also relates to a process for the qualitative and/or quantitative determination of anions, according to which the salts containing the anions to be determined or the solutions of these salts are brought into contact with solutions of the fluoromethylated polycyanobenzenes of the formula I.

The contacting of salts with fluoromethylated polycyanobenzenes of the formula I gives rise to strongly coloured salt-like adducts which may be fluorescent or absorb in UV light and whose light or UV absorption is substantially determined by the anion complexes formed by the adduct of the anions of the salt with the fluoromethylated polycyanobenzenes of the formula I.

Examples of suitable representatives of the fluoromethylated polycyanobenzenes of the formula I to be used according to the invention are: pentacyanotrifluoromethylbenzene, 1,2,4,5-tetracyano-3,6-bis(trifluoromethyl)benzene, pentacyanodifluoromethylbenzene and pentacyanochlorodifluoromethylbenzene.

For the detection and determination of the anions, the fluoromethylated polycyanobenzenes of the formula I can be used in the form of 0.1 to 5% strength by weight solutions in organic solvents, such as acetonitrile, or mixtures of organic and inorganic solvents, such as acetonitrile and water.

The fluoromethylated polycyanobenzenes of the formula I to be used according to the invention as test reagents are suitable in particular for visible detection of anions after their separation by paper, thin-layer or ion chromatography.

A 1% strength by weight solution of pentacyanotrifluoromethylbenzene in acetonitrile gives the following colorations with salts of inorganic acids: an orange, fluorescent coloration with potassium cyanide,
a red coloration with potassium thiocyanate,
a yellow, fluorescent coloration with sodium cyanate.

A 1% strength by weight solution of pentacyanotrifluoromethylbenzene in an acetonitrile/water (1:1 parts by volume) mixture gives the following colorations with salts of inorganic acids:
yellow, fluorescent colorations with sodium fluoride, sodium chloride and potassium bromide,
a violet coloration with potassium iodide, orange, fluorescent colorations with sodium carbonate, sodium hydroxide and sodium sulphate;
a yellow, fluorescent coloration with sodium sulphate,
a deep red coloration with sodium sulphite,
yellow colorations with sodium nitrate and sodium nitrite, and
red colorations with disodium phosphate and sodium hypophosphite.

A 1% strength by weight solution of pentacyanotrifluoromethylbenzene in an acetonitrile/water (1:1 parts by volume) mixture gives yellow, fluorescent colorations with salts of organic acids, for example salts of carboxylic acids, such as sodium formate, sodium acetate, sodium tartrat and sodium oxalate.

It is true that in general the ammonium salts give more weakly coloured adducts with the fluoromethylated polycyanobenzenes of the formula I than the corresponding sodium salts; however, since these adducts of the ammonium salts with the compounds of the formula I have strong absorption in the UV region, the visual detection of the ammonium salts by means of the fluoromethylated polycyanobenzenes of the formula I to be used according to the invention is also very strong.

The anions are detected and determined after the chromatographic separation on the basis of their coloration in visible light or their fluorescence under UV chromatograms can be sprayed with the fluoromethylated polycyanobenzenes of the formula I to be used according to the invention. In ion chromatography, the solutions of the test reagents to be used according to the invention can be added to the eluent from the separating column, after the separation of the ions has been completed.

Percentages in the examples which follow are by weight.

EXAMPLE 1

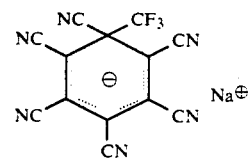

24.5 g (0.5 mol) of sodium cyanide are added to a solution of 24.3 g (0.1 mol) of α,α,α,2,3,5,6-heptafluoro-p-tolunitrile (J. Org. Chem. 33, 1658) in 250 ml of dry acetonitrile with stirring and exclusion of moisture, and the mixture is stirred at room temperature for 10 days.

It is then filtered, the residue is washed with acetonitrile, and the filtrate is concentrated in a rotary evaporator up to a bath temperature of about 30° C. To remove any remaining unreacted heptafluoro compound, the concentrated filtrate is stirred together with 250 ml of dry dichloromethane at room temperature, filtered, the residue is washed with dichloromethane and dried, giving 31.0 g (96.8% of theory) of the orange-red sodium salt of the abovementioned structure.

Elemental analysis: $C_{13}F_3N_6Na$:
calculated: C 48.77%, F 17,80%, N 26.25%, Na 7.18%.
found: C 48.5%, F 17.2%, N 26.4%, Na 7.0%.
IR (KBr) in cm: 2224, 2205, 1563, 1472, 1412, 1359, 1241, 1206, 1175, 1148, 937, 729.
UV/vis (DMF):
$\nu_{max} = 19.400$ cm$^{-1}$.
$\lambda_{max} = 515.5$ nm.
$\epsilon_{max} = 12.200$.
75.39 MHz $^{19}$F NMR (d$_6$-acetone):
$\delta CF_3 = 2.76$ ppm, relative to $CF_3$-COOH (external)
125.77 MHz $^{13}$C NMR (d$_6$-acetone):

| δ (ppm) | |
|---|---|
| 126.089 | C-3, C-5 |
| 124.323 | CF$_3$: $J_{CF} = 290.9$ Hz (q) |
| 116.779 | |
| 116.079 | |
| 113.910 | CN |
| 112.745 | |
| 83.309 | C-4 |
| 78.812 | C-2, C-6 |
| 50.623 | C-1: $^3J_{CF} = 33.67$ Hz (q) |

Fluorence spectrum (DMF):
max. emission at: 16,900 cm$^{-1}$,
max. excitation at: 19,400 cm$^{-1}$,
max. excitation at: 19,400 cm$^{-1}$,
Δ Stokes: 2,500 cm$^{-1}$,
quantum yield: 0.62.

EXAMPLE 2

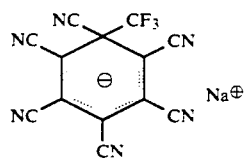

Example 1 is repeated, except that the reaction is carried out under reflux instead of at room temperature. After about 20 hours, the reaction is virtually finished. The sodium salt is obtained in a yield of also more than 95% of theory.

EXAMPLE 3

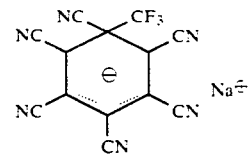

23.0 g (469 mmol) of sodium cyanide are added to a solution of 28.5 g (117 mmol) of α,α,α,2,3,5,6-heptafluoro-p-tolunitrile in 285 ml of dry acetonitrile with stirring and exclusion of moisture, and the mixture is stirred at room temperature for 8 days. The work up is as described in Example 1, giving 28.2 g (94% of theory, relative to the sodium cyanide used) of the sodium salt of the abovementioned structure.

EXAMPLE 4

29.4 g (0.6 mol) of sodium cyanide are added to a solution of 23.6 g (0.1 mol) of pentafluorotrifluoromethylbenzene in 250 ml of dry acetonitrile with stirring and exclusion of moisture, and the mixture is stirred at room temperature for 12 days. The work up is as described in Example 1.

20.8 g (65% of theory) of the sodium salt of the above-mentioned structure are obtained.

EXAMPLE 5

1.00 g (3.125 mmol) of the sodium salt $C_{13}F_3N_6Na$ obtained according to Example 1 is dissolved in 5 g of acetic acid. The solution is allowed to stand at room temperature for 12 hours, 50 ml of water are added, the precipitate formed is filtered off, washed with water and dried. Yield: 0.78 g (92.1% of theory) of pentacyanotrifluoromethylbenzene. The compound does not yet melt at 270° C.; it can be sublimed at 200°–220° C./0.1 mbar without decomposition.
IR (KBr) in cm$^{-1}$: 2250, 1561, 1419, 1327, 1290, 1263, 1204, 1181, 997, 853, 839, 792, 731, 697.
75.39 MHz $^{19}$F NMR (d$_6$-DMSO):
$\delta CF_3 = -19.95$ ppm relative to $CF_3$-COOH (external)
125.77 MHz $^{13}$C NMR (d$_6$-DMSO):

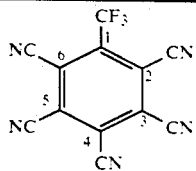

| δ (ppm) | |
|---|---|
| 136.583 | C-1; $^3J_{CF}$ = 33.93 Hz (q) |
| 125.292 | C-3, C-5 |
| 123.449 | C-4 |
| 119.527 | CF$_3$; $J_{CF}$ = 277.74 Hz (q) |
| 118.968 | C-2, C-6; $^4J_{CF}$ = 1.81 Hz (q) |
| 111.992 | 2 CN on C-2 / C-6 or C-3 / C-5 |
| 111.595 | CN on C-4 |
| 111.187 | 2 CN on C-3 / C-5 or C-2 / C-6 |

EXAMPLE 6

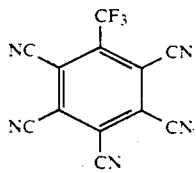

60.5 g (189 mmol) of the sodium salt $C_{13}F_3N_6Na$ prepared according to Example 1 are stirrred together with about 1.5 liters of 1N aqueous hydrochloric acid solution at room temperature for 24 hours. The precipitate is then filtered off, washed with water and dried.

Yield: 48.1 g (93.8% of theory) of pentacyanotrifluoromethylbenzene, which is identical with the compound obtained according to Example 5.

EXAMPLE 7

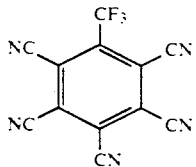

1.00 g (3.125 mmol) of the sodium salt $C_{13}F_3N_6Na$ obtained according to Example 1 is heated in a sublimation apparatus at 220° C./0.1 mbar for 24 hours.

0.57 g (67.3% of theory) of pentacyanotrifluoromethylbenzene is obtained, which is identical to the compound obtained according to Example 5.

EXAMPLE 8

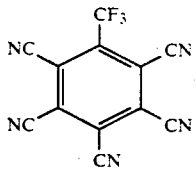

2.53 g (51.6 mmol) of sodium cyanide are added to a solution of 2.43 g (10 mmol) of α,α,α,2,3,5,6-heptafluoro-p-tolunitrile in 25 ml of dry dimethylformamide with stirring and exclusion of moisture, as a result of which the reaction mixture heats up and immediately turns a red colour. It is stirred overnight and then poured into a mixture of 200 ml of water and 50 ml of conc. hydrochloric acid. After stirring at room temperature for 24 hours, the precipitate is filtered off, washed with water and dried.

Yield: 2.19 g (80.1% of theory) of pentacyanotrifluoromethylbenzene, which is identical to the product obtained according to Example 5.

EXAMPLE 9

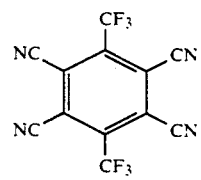

4.90 g (100 mmol) of sodium cyanide are added to a solution of 5.72 g (20 mmol) of 1,2,4,5-tetrafluoro-3,6-bis(trifluoromethyl)benzene in 100 ml of dry dimethylformamide with stirring and exclusion of moisture, as a result of which the reaction mixture heats up and immediately forms a red solution. It is initially cooled with ice water, and then stirring at room temperature is continued overnight. The reaction mixture is then poured into a mixture of 500 ml of water and 500 ml of concentrated hydrochloric acid with stirring. Stirring is continued for 1 hour, the precipitate is filtered off and After drying, 4.95 g (78.8% of theory) of 1,2,4,5-tetracyano-3,6-bis(trifluoromethyl)benzene are obtained. The compound does not yet melt at 270° C.; it can be sublimed at 200° C./0.1 mbar without decomposition.

IR (KBr) in cm : 2253, 1444, 1422, 1314, 1206, 1180, 1136, 856, 678.

EXAMPLE 10

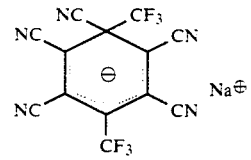

3.92 g (80 mmol) of sodium cyanide are added to a solution of 5.72 g (20 mmol) of 1,2,4,5-tetrafluoro-3,6-bis(trifluoromethyl)benzene in 80 ml of dry acetonitrile with stirring and exclusion of moisture, and the mixture is stirred at room temperature for 10 days. The reaction mixture is then worked up as described in Example 1.

3.40 g (58.6% of theory, relative to the sodium cyanide used) of the red sodium salt $C_{13}F_6N_5Na$ of the above-mentioned structure are obtained.

IR (KBr) in cm$^{-1}$: 2206, 1544, 1431, 1378, 1292, 1239, 1207, 1146, 1009, 892, 730.

UV/vis (DMF):

$\nu_{max}$ = 20,100 cm$^{-1}$, $\lambda_{max}$ = 497.5 nm, $\epsilon$max = 8,300.

EXAMPLE 11

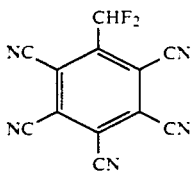

12.25 g (0.25 mol) of sodium cyanide are added to a solution of 10.9 g (0.05 mol) of difluoromethylpentafluorobenzene in 200 ml of dry dimethylformamide which had been cooled to about −40° C. with stirring and exclusion of moisture. After as little as 5–10 minutes and at an internal temperature of −40° C., the reaction mixture has a strong orange-red colour. Stirring at temperatures below 0° C. is continued for another 2 hours; the reaction mixture is then allowed gradually to warm to room temperature overnight and is stirred at room temperature for another 10 days. The reaction mixture is then poured into about 2 liters of 1N hydrochloric acid. The mixture is stirred at room temperature overnight. The precipitate is then filtered off, washed with water and dried.

Difluoromethylpentacyanobenzene is obtained in good yield; it does not yet melt at 270° C. and can be sublimed at 200° C./0.1 mbar without decomposition.

$^1$H-NMR (d$_6$-DMSO): δ=7.6 ppm (t, J=50.0 Hz).

IR (KBr) in cm$^{-1}$: 2248, 1565, 1431, 1378, 1343, 1307, 1277, 1136, 1077, 1043, 896, 834, 790, 704, 627.

EXAMPLE 12

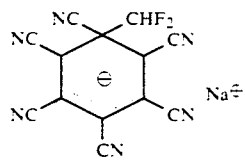

The procedure of Example 4 is repeated, except that 21.8 g (0.1 mol) of difluoromethylpentafluorobenzene are used instead of 0.1 mol of pentafluorotrifluoromethylbenzene, giving the orange-red sodium salt C$_{13}$HF$_2$N$_6$Na of the abovementioned structure in good yield.

IR (KBr) in cm$^{-1}$: 2198, 1563, 1476, 1406, 1356, 1239, 1206, 1128, 1088, 748, 728.

UV/vis (DMF):
$v_{max}$=19,350 cm$^{-1}$
$\lambda_{max}$=516.8 nm
$\epsilon_{max}$=9,400

EXAMPLE 13

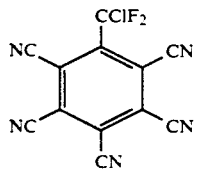

The procedure of Example 11 is repeated, except that 12.63 g (0.05 mol) of chlorodifluoromethylpentafluorobenzene are used instead of 0.05 mol of difluoromethylpentafluorobenzene.

Chlorodifluoromethylpentacyanobenzene is obtained, which does not yet melt at 270° C. and can be sublimed at 200° C./0.1 mbar without decomposition.

IR (KBr) in cm$^{-1}$: 2247, 1415, 1310, 1283, 1161, 1018, 921, 846, 792, 753, 669, 623.

WORKING EXAMPLES

WORKING EXAMPLE 1

2 μl of solutions containing 10, 20, 50, 100, 200, 500 mg each per 100 ml of solution of malonic acid, succinic acid, glutaric acid, adipic acid, suberic acid and sebacic acid in i-propanol:water=4:1 parts by volume are spotted on a cellulose plate (for example from Merck Art. No. 5786).

Chromatographic separation is carried out by development with n-propanol:methanol:25% strength aqueous ammonia =6:1:3 parts by volume.

After spraying wit a 1% strength solution of pentacyanotrifluoromethylbenzene (from Example 5) in acetonitrile, the acids present in the form of ammonium salts can be detected under UV light (366 nm). Detection limit: 1 μg. In this manner, the following R$_f$values were determined for the individual acids: 0.16 for malonic acid; 0.27 for succinic acid; 0.32 for glutaric acid; 0.39 for adipic acid; 0.45 for suberic acid and 0.53 for sebacic acid.

In contrast to the coloration of anions using methyl red, which disappears after as little as a few minutes, the anions, after coloration with pentacyanotrifluoromethylbenzene, remain visible under UV for days.

WORKING EXAMPLE 2

Solutions of formic acid, acetic acid and propionic acid in acetone are spotted on a cellulose plate (for example from Merck, Art. No. 5786). The amounts applied contain in each case 3 μg, 4 μg, 10 μg, 20 μg and 40 μg of each acid.

Chromatographic separation is carried out by development with n-propanol:methanol:25% strength aqueous ammonia=6:1:3 parts by volume.

After spraying with a 1% strength solution of pentacyanotrifluoromethylbenzene in acetonitrile, the acids which are present in the form of ammonium salts can be detected under UV light (366 nm).

The detection limits for the individual acids are: 20 μg for formic acid, 4 μg for acetic acid and 2 μg for propionic acid. The following R$_f$ values were determined for the individual acids: 0.47 for formic acid, 0.52 for acetic acid and 0.56 for propionic acid.

WORKING EXAMPLE 3

2 μl each of a 1% strength solution of sodium chloride, sodium bromide, sodium iodide and potassium isocyanate are spotted on paper, for example from Schleicher & Schüll, No. 2040 b.

Chromatographic development is carried out with butanol:pyridine:25% strength aqueous ammonia =2:1:2 parts by volume.

After spraying with a 1% strength solution of pentacyanotrifluoromethylbenzene in acetonitrile a yellow spot appears in each case at the R$_f$value of 0.2, which is due to NaOH or KOH. Further spots can be detected in UV light (366 nm), namely at an R$_f$of 0.32 for chloride, 0.43 for bromide, 0.54 for iodide and 0.62 for thiocyanate.

If the separation is carried out on a cellulose plate, the R$_f$ values are 0.46 for chloride, 0.55 for bromide, 0.66 for iodide and thiocyanate. Sulphate (R$_f$ value 0.32) and sulphide (R$_f$ value 0.36) can also be detected on the cellulose plate.

WORKING EXAMPLE 4

Solutions of chloroacetic acid, glycolic acid, formic acid and malonic acid are spotted on a silica gel plate, for example silica gel 60 without fluorescence indicator (Merck Art. No. 5721). The amounts applied contain 1 μg, 5 μg, 10 μg and 50 μg of each acid.

Chromatographic development is carried out in a sandwich chamber using methanol:ethanol:i-propanol:i-butanol:10% strength aqueous ammonia —10:15:20:30:25 parts by volume.

After spraying with a 1% strength solution of pentacyanotrifluoromethylbenzene in acetonitrile, the acids which are present in the form of ammonium salts can be detected under UV light (366 nm) down to 1 μg. The R$_f$ values are: 0.16 for malonic acid, 0.36 for chloroacetic acid, 0.44 for glycolic acid and 0.59 for aminoacetic acid.

WORKING EXAMPLE 5

2 and 10 μl each of 0.1% strength aqueous solutions of sodium sulphite, sodium sulphate, sodium thiosulphate and sodium sulphide are spotted on a cellulose plate, for example from Merck, Art. No. 5786.

Chromatographic separation is carried out by development with butanol:pyridine:25% strength aqueous ammonia=2:1:2 parts by volume.

After spraying with a 1% strength solution of pentacyanotrifluoromethylbenzene in acetonitrile, sodium sulphite and sodium thiosulphate show up as red and brown spots respectively (detection limit 2 μg), sodium sulphide as a yellow spot (detection limit 10 μg); sodium sulphate can be detected under UV light (detection limit 10 μg).

We claim:

1. Fluoromethylated polycyanobenzenes of the formula

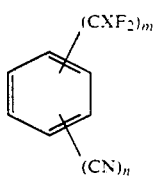
(I)

in which
X represents hydrogen, fluorine or chlorine,
m is 1 or 2 and
n is (6−m).

2. Salt-like adducts of the formula

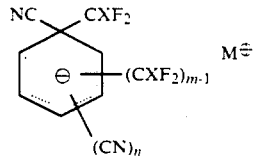
(III)

in which
X represents hydrogen, fluorine or chlorine,
m is 1 or 2,
n is (6−m) and
m⊕ represents an alkali metal cation.

3. Fluoromethylated polycyanobenzenes according to claim 1, in which m is 1.

4. Fluoromethylated polycyanobenzenes according to claim 1, in which m is 2.

5. A process for the preparation of a fluoromethylated polycyanobenzene according to claim 1, which comprises reacting a fluoromethylated fluorobenzene of the formula

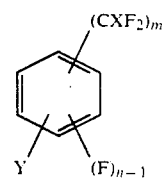
(II)

in which
Y represents fluorine or CN,
with an alkali metal cyanide in an organic diluent to give a salt-like adduct of the formula

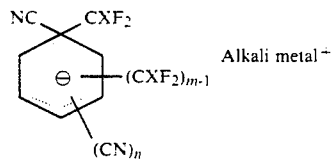
(III)

and reacting the adduct with an acid or heating it to a temperature of 150°–300° C.

* * * * *